US00PP09309P

United States Patent [19]

Meilland

[11] Patent Number: Plant 9,309

[45] Date of Patent: Oct. 3, 1995

[54] HYBRID TEA ROSE PLANT NAMED 'MEIQUALIS'

[75] Inventor: Alain A. Meilland, Antibes, France

[73] Assignee: The Conard-Pyle Company, West Grove, Pa.

[21] Appl. No.: 356,622

[22] Filed: Dec. 15, 1994

[51] Int. Cl.[6] ..... A01H 5/00

[52] U.S. Cl. ..... Plt./20

[58] Field of Search ..... Plt./20, 21

[56] References Cited

U.S. PATENT DOCUMENTS

P.P. 4,738 6/1981 Weeks ..... Plt./20

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which abundantly forms attractive bright double long-lasting dark velvet-red blossoms. The foliage is dark green and glossy and contrasts well with the blossom coloration. Long erect stems are formed that infrequently bear thorns. The new variety is particularly suited for cut-flower production under greenhouse growing conditions. Additionally, the new plant exhibits very good disease resistance.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the product of the cross of the Meinical variety (non-patented in the United States) and the Meired variety (U.S. Plant Pat. No. 3,452). The Meired variety sometimes is known as the Visa variety. The male parent (i.e., the pollen parent) of the new variety was the product of the pollination of the Meiduitra variety (non-patented in the United States) and the Madelon variety (U.S. Plant Pat. No. 5,820). The Madelon variety is also known as the Ruimeva variety. The parentage of the new variety can be summarized as follows:

(Meinical×Meired)×(Meiduitra×Madelon)

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance attractive bright double long-lasting dark velvet-red blossoms, (b) forms attractive dark green glossy foliage, (c) forms long erect stems that infrequently bear thorns, and (d) is particularly suited for cut flower production.

The new variety well meets the needs of the horticultural industry and is particularly well suited for use when producing cut flowers under greenhouse conditions.

The new variety has been found to undergo asexual propagation in France by a number of routes, including budding, grafting, and cuttage. The characteristics of the new variety have been found by such methods in France to be stable and to be strictly transmissible from one generation to another.

The new variety has been named the Meiqualis variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during June while budded on *Rosa indica* understock and growing in greenhouses at Le Cannet des Maures, France.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface; and FIG. 15—illustrates a specimen of a leaf with seven leaflets—plan view—under surface.

DETAILED DESCRIPTION

Figures 1, 2, 3, 4, 5, 6, 7, 8, 9, 10, 11, 12, 13, 14, 15:
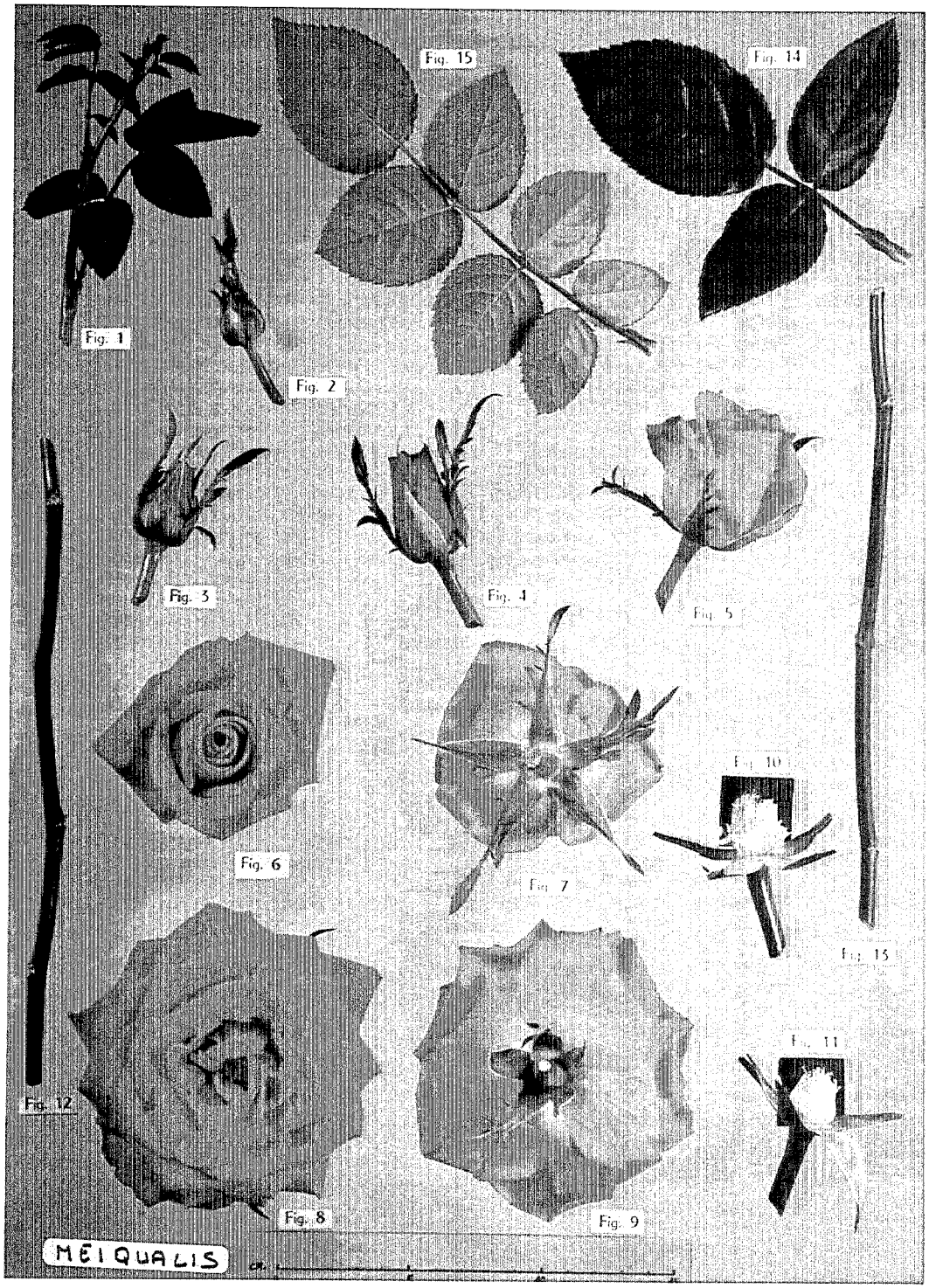

The chart used in the identification of the colors is that of The Royal Horticultural Society (R.H.S. Colour Chart). The description is based on the observation of two year-old plants while budded on *Rosa indica* understock and growing during September in greenhouses at Le Cannet des Maures, France. The coloration in common terms precedes reference to the chart.

Class: Hybrid Tea.

Plant:

*Height.*—Approximately 60 to 80 cm. on average at the end of the growing season.

*Habit.*—Erect.

Branches:

*Color.*—Young stems: dark green, Green Group 137A. Adult wood: Scheele's Green, Green Group 143A.

*Thorns.*—Size: small. Quantity: rarely are exhibited, and occur on adult wood when present. Color: greenish.

Leaves:

*Stipules.*—Adnate, pectinate, wide and linear.

*Petioles.*—Upper surface; striped reddish brown on young foliage, medium green on adult foliage, and more or less glandular. Under surface: light green and bear a few small thorns.

*Leaflets.*—Number: 3, 5, and 7. Shape: oval. Serration: simple and regular. Texture: consistent. General appearance: dense and glossy foliage. Color (young foliage): upper surface: dark green, Green Group 137A, and widely suffused with reddish-brown. under surface: lighter green, Green Group 137B, and widely suffused with reddish-brown. Color (adult foliage): upper surface: dark green, Green Group 137A, and suffused with Scheele's Green, Green Group 143A. under surface: light green, Green Group 139C, and suffused with light grey green, Greyed-Green Group 191A.

Inflorescence:

*Number of flowers.*—Usually one flower per stem.

*Peduncle.*—Medium green and sometimes bears a few thorns. The length is approximately 10 to 11 cm. on average.

*Sepals.*—Upper surface: tomentose, and greenish in coloration. Under surface: light green, edges are commonly very appendiculated.

*Buds.*—Shape: conical. Length: approximately 3 to 4 cm. on average. Size: medium. Color upon opening: upper surface: Currant Red, Red Group 46A, and sometimes with white marbling. under surface: Cardinal Red, Red Group 53B.

*Flower.*—Shape: cup-shaped. Diameter: approximately 9 to 10 cm. on average. Color (when opening begins): upper surface: Strawberry Red, Red Group 46B, and suffused with Cardinal Red, Red Group 53C. under surface: Cardinal Red, Red Group 53B. Color (when blooming): upper surface: Strawberry Red, Red Group 46B, and suffused with Cardinal Red, Red Group 53C. under surface: Cardinal Red, Red Group 53B, and lighter at the base. Color (at end of opening): upper surface: Strawberry Red, Red Group 46B, and suffused with Cardinal Red, Red Group 53C. under surface: Cardinal Red, Red Group 53B, and lighter at the base. Fragrance: none. Lasting quality: very long when cut and placed in a vase. Petal number: approximately 40 on average. Petal shape: outer petals tend to be rounded with a cordiform base, and the inner petals tend to be oval with a cuneiform base. Petal drop: very good. Stamen number: approximately 22 on average. Anthers: normal, and ochre in coloration. Filaments: light fuchsia in coloration. Pistils: approximately 16 to 20 on average. Stigmas: normal, and commonly display a vegetative center. Styles: fuchsia in coloration, very short, and tomentose at base. Receptacle: medium green, smooth, and in longitudinal section in the shape of a tube.

Development:

*Vegetation.*—Strong.

*Blooming.*—Abundant.

*Resistance to diseases.*—Very good.

I claim:

1. A new and distinct variety of Hybrid Tea rose plant characterized by the following combination of characteristics:

(a) forms in abundance attractive bright double long-lasting dark velvet-red blossoms, (b) forms attractive dark green glossy foliage, (c) forms long erect stems that infrequently bear thorns, and (d) is particularly suited for cut flower production;

substantially as herein shown and described.

* * * * *

MEIQUALIS